United States Patent [19]

Perna

[11] Patent Number: 4,694,506
[45] Date of Patent: Sep. 22, 1987

[54] FOLDABLE EYESHADE

[76] Inventor: Fred P. Perna, 1417 West Park, Anaconda, Mont. 59711

[21] Appl. No.: 19,249

[22] Filed: Feb. 26, 1987

[51] Int. Cl.⁴ .............................................. A61F 9/04
[52] U.S. Cl. ............................................ 2/12; 2/200
[58] Field of Search ..................... 2/12, 200, 195, 196, 2/209.1, 171, 175, 177

[56] References Cited

U.S. PATENT DOCUMENTS

| | | | |
|---|---|---|---|
| 1,198,337 | 9/1916 | Folsom | 2/12 |
| 1,599,576 | 9/1926 | Mahony | 2/12 |
| 1,732,357 | 10/1929 | Davis | 2/12 |
| 2,765,472 | 10/1956 | Schoen-Wolski | 2/200 X |

FOREIGN PATENT DOCUMENTS 0096878 9/1939 Sweden .................................... 2/12

Primary Examiner—Peter Nerbun
Attorney, Agent, or Firm—Peterson, Wicks, Nemer & Kamrath

[57] ABSTRACT

The eyeshade includes a headband and a visor of flexible sheet material, such as cardboard, each having aligned, centrally disposed fold lines. The visor additionally has two pairs of acutely angled fold lines that are laterally spaced from the centrally disposed fold lines on the visor. By means of specially shaped and properly located pressure-sensitive tape sections, the visor is hingedly connected to the headband. The various fold lines enable the eyeshade to be folded into a sufficiently compact condition such that it can be carried in one's pocket or purse, yet readily unfolded to shield the user's eyes.

15 Claims, 10 Drawing Figures

FOLDABLE EYESHADE

BACKGROUND OF THE INVENTION

1. Field of the Invention

This invention relates generally to eyeshades, and pertains more particularly to a foldable eyeshade that can be collapsed into a sufficiently compact condition so that it can be carried in one's pocket or purse.

2. Description of the Prior Art

Collapsible eyeshades, of course, are not entirely unique. As a matter of fact, a number of rather complex eyeshades of a foldable character have been patented. In my opinion, the one coming the closest to my eyeshade is disclosed in U.S. Pat. No. 1,718,867, issued on June 25, 1929 to Sophy Mahlmann for "FOLDABLE EYESHADE WITH CAP." In this instance, an accordion-like visor is secured at its upper edge to the lower front and side edges of a fabric cap. However, owing to the requirement that a fabric cap be provided, the overall cost of the eyeshade and cap becomes quite appreciable. This, in my view, is a decided drawback as far as the patented eyeshade and cap is concerned.

SUMMARY OF THE INVENTION

Accordingly, an important object of my invention is to provide a foldable eyeshade that can be collapsed into such a compact form that it can be readily placed in a person's pocket or purse. Also, the invention has for an aim the easy retrieval of the collapsed eyeshade inasmuch as a portion thereof is made readily accessible for grasping by the user's fingers. Also, it is within the comtemplation of the invention to manufacture and market my eyeshade in a completely collapsed condition, thereby facilitating the packaging and shipping thereof.

Another object of the invention is to provide an eyeshade that will be relatively inexpensive, especially inasmuch as it can be fabricated from low-cost sheet material, such as cardboard. While the eyeshade will be sufficiently inexpensive so that it can be, if desired, discarded after but a single use, my eyeshade can be reused a number of times.

The invention has for another object the provision of an eyeshade that will be quite attractive, thereby encouraging its widespread use. As far as its aesthetic values are concerned, an eyeshade fabricated in accordance with my invention has no gaps or spaces which would detract from its overall appearance. Also, it has two foldable pleats that produce different panel levels, thereby enhancing the appearance of the eyeshade. Furthermore, owing to the employment of pressure-sensitive tape, the components of my eyeshade can be fabricated of contrastingly different colors. More specifically, the tape can be one color, the headband a different color and the visor a still different color.

Yet another object of my invention is to provide an eyeshade having sufficient areas thereon so that various advertising or promotional messages may be printed on the visor and/or headband.

Still further, an object of the invention is to provide an eyeshade, even though completely collapsible, that will be of an effective size so as to appropriately shield the user's eyes from the sun or artificial lights, even though the light rays may come over a relatively great angular range.

Still another object of the invention is to provide a collapsible eyeshade that will be comfortable to wear.

Another object is to provide an eyeshade that readily conforms to heads of different size, thereby enabling only one size of eyeshade to be marketed.

Briefly, my invention envisages a completely foldable eyeshade that can be made from paper stock, such as that commonly used for postcards. Initially, two blanks are die cut so that one blank provides a headband that extends approximately halfway around the user's head. The headband has a centrally located weakened fold line. The other blank forms the visor, and it likewise has a central fold line. However, the visor has two pairs of additional fold lines—each pair constituting two acutely angled fold lines having their apexes adjacent the lower edge of the headband. The headband assumes a curved relation, corresponding to the shape of the forehead of the user, and when so curved it provides a curved lower edge. The upper edge of the visor is concavely curved so as to complement the curvature of the headband's lower edge. A series of gummed or pressure-sensitive tape sections are specifically configured and located so as not to interfere with the collapsibility of the eyeshade.

DESCRIPTION OF THE PREFERRED EMBODIMENT

Figure 1:
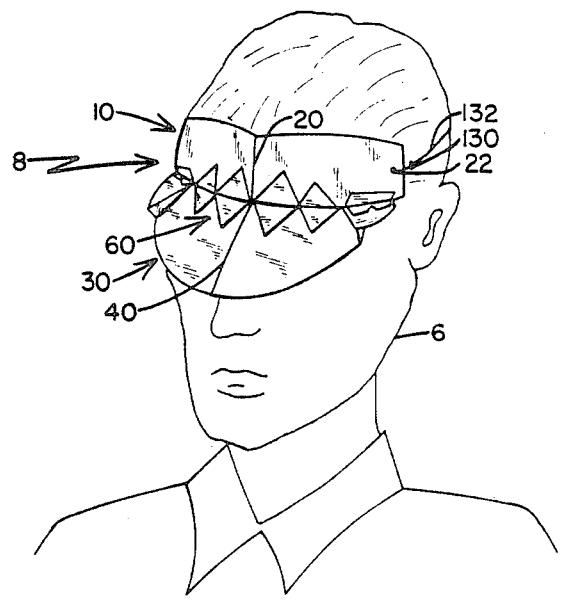
FIG. 1 is a perspective view of my eyeshade when in actual use.
Figure 2:
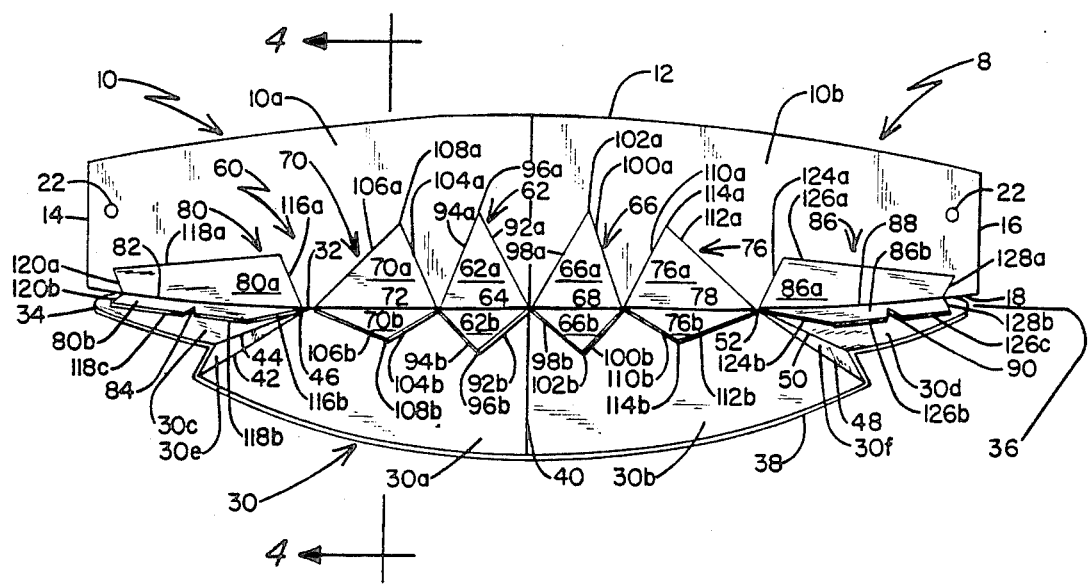
FIG. 2 is a front elevational view of the eyeshade without the person's head being included.
Figure 3:
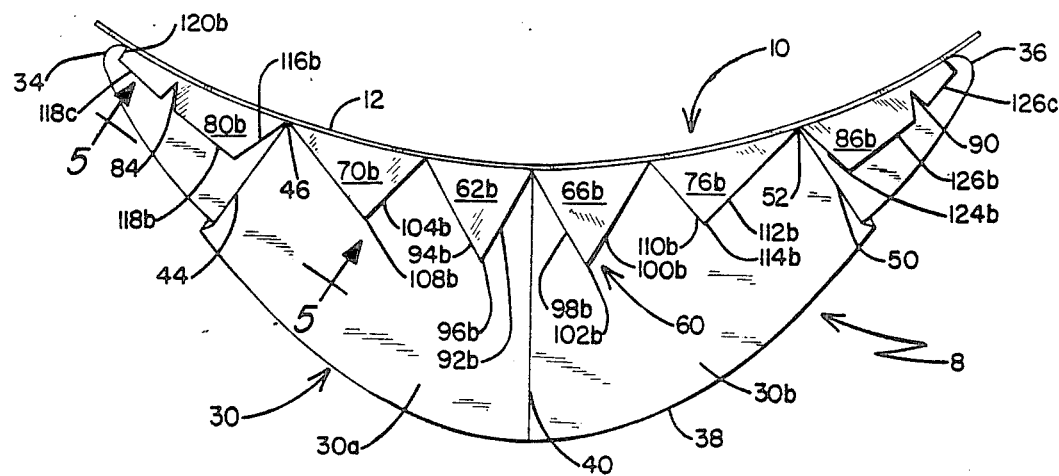
FIG. 3 is a top plan view of the eyeshade.
Figure 4:
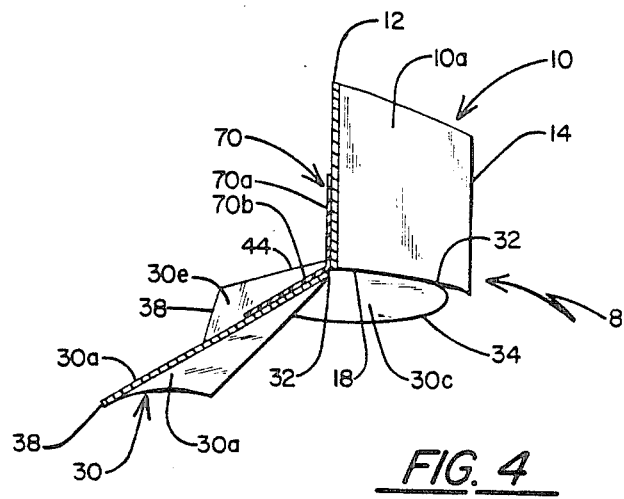
FIG. 4 is a sectional view taken in the direction of line 4—4 of FIG. 2.
Figure 5:
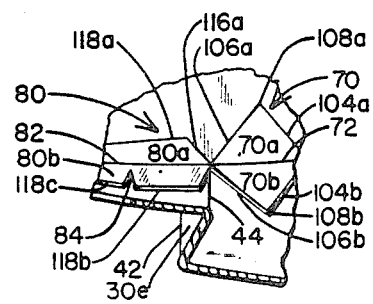
FIG. 5 is a sectional detail taken in the direction of line 5—5 of FIG. 3.

Referring first to FIG. 1, a person's head 6 has been illustrated when using my eyeshade which has been denoted generally by the reference numeral 8. The eyeshade 8 comprises a headband 10 having an upper edge 12, a left side edge 14, a right side edge 16, and a lower, convexly curved edge 18. Later, it will be seen when discussing FIG. 8, that the lower edge 18, while convexly curved when the eyeshade 8 is in use, constitutes a straight edge on the die-cut blank forming the headband 10. It should be noticed at this stage, though, that the headband 10 has a central weakened fold line 20. In this way, there are formed a panel 10a at the left and a panel 10b at the right. The panels 10a and 10b thus constitute the headband 10. As best viewed in FIG. 2, the headband 10 has a pair of holes 22, there being one at the opposite ends of the two panels 10a and 10b. The reason for the holes 22 will become manifest hereinafter.

Attention is now directed to a visor 30 having an upper concavely curved edge 32, a rounded edge 34 at its left end, a rounded edge 36 at its right end, and a convexly curved lower edge 38. It is the curvature of the upper edge 32 that is important; in this regard, it complements the curvature of the lower edge 18 of the headband 10. As with the headband 10, the visor 30 has a central weakened fold line 40. When assembled, the two fold lines 20 and 40 are in a longitudinal alignment with each other.

Whereas the headband 10 has only the single fold line 20, the visor 30 has two pairs of fold lines in addition to its fold line 40. In this regard, one pair of such additional fold lines includes the fold lines 42 and 44 which are at an acute angle with each other, the apex 46 thereof being adjacent a portion of the upper concavely curved edge 32. The other pair of acutely angled fold lines have been given the reference numerals 48 and 50, having their apex 52 located adjacent another portion of the upper concavely curved edge 32.

From the foregoing, it will be discerned that the various fold lines 40, 42, 44, 48, and 50 form various panels, as far as the visor 30 is concerned. More specifically, the central fold line 40 and the angled fold line 42 form the panel 30a, whereas the central fold line 40 in conjunction with the angled fold line 48 forms the panel 30b. What will be termed a wing panel 30c is formed by the angled fold line 44 in conjunction with the rounded left edge 34. Similarly, the wing panel 30d is formed by the angled fold line 50 and the rounded right edge 36. Additionally, the acutely angled fold lines 42 and 44 form an intermediate triangular panel 30e, and the angled fold lines 48 and 50 form a similar triangularly configured panel 30f.

Acting both functionally and aesthetically are the triangular panels 30e and 30f which cause the panels 30a and 30b to slope downwardly at a greater angle with respect to the headband 10 than do the wing panels 30c and 30d. This condition prevails during the time that my eyeshade 8 is being worn. However, as will become clearer hereinafter, all of the fold lines 20, 40, 42, 44, 48 and 50 coact to permit the eyeshade 10 to be folded into what amounts to a compact planar condition.

A series of gummed or pressure-sensitive tape sections have been collectively given the reference numeral 60. The collection 60 includes a first individual tape section 62 comprised of an upper triangular portion 62a and a lower triangular portion 62b. There is a fold line at 64 between the portions 62a and 62b. A similar gummed or pressure-sensitive tape section 66 is located at the right of the fold line 40, being comprised of an upper triangular portion 66a and a lower triangular portion 66b. A fold line 68 corresponds to the fold line 64.

More to the left is another gummed or pressure-sensitive tape section 70, being composed of an upper triangular portion 70a and a lower triangular portion 70b with a fold line 72 therebetween. Similar to the tape section 70 is a tape section 76 at the right, the section 76 being comprised of an upper triangular portion 76a and a lower triangular portion 76b with a fold line 78 therebetween.

Still additional gummed tape sections 80 and 86 are provided. The section 80 includes an upper portion 80a and a lower portion 80b, there being a fold line 82 therebetween. It should be observed that the lower portion 80b has a notch 84 formed therein. Similarly, the section 86 includes an upper portion 86a and a lower portion 86b, there being a fold line 88 therebetween. The lower portion 86b has a notch 90 formed therein.

Recapitulating, the tape sections 62 and 70 span the distance between the central fold line 40 and the apex 46, whereas the tape sections 66 and 76 span the distance between the fold line 40 and the apex 52. The sections 80 and 86 extend outwardly from the apices 46 and 52 to the left and right ends, respectively, of the headband 10 and the visor 30.

Although the material constituting the headband 10 and the visor 30 has not yet been described, it can be pointed out that the various tape sections 62, 66, 70, 76, 80, and 86 are configured so as to retain the headband 10 and 30 together, yet permit a sufficient amount of flexing in a three-dimensional relationship so as to conform to the shape of the user's head 6 and at the same time permit the eyeshade 8 to be completely folded into a compact condition when not in use.

Although perhaps not necessary to label all of the edges of the various tape sections, it is believed desirable to do so. With this in mind, it is to be observed that the portion 62a of the tape section 62 is formed by the edges 92a and 94a converging to a point or apex at 96a, whereas the portion 62b has the edges 92b and 94b coming to a point or apex at 96b. Similarly, the triangular portion 66a belonging to the tape section 66 has the edges 98a and 100a forming the point 102a, whereas the portion 66b of the section 66 has the edges 98b and 100b forming the point 102b. The portion 70a of the tape section 70 has the edges 104a and 106a forming the point 108a, whereas its portion 70b has the edges 104b and 106b which result in the point 108b. By the same token, the portion 76a of the tape section 76 has the edges 110a and 112a forming the point or apex 114a, whereas the portion 70b has the edges 110b and 112b forming the point 114b.

It will be appreciated that by having the points 96a, 96b, 102a, 102b, 108a, 108b, 114a and 114b, the material constituting the tape collection 60 provides an adequate securement of the visor 30 to the headband 10, doing so throughout the lengths of their fold lines 64, 68, 72, and 78. The narrowing of the various triangular portions by reason of the points or apices 96a, 96b, 102a, 102b, 108a, 108b, 114a, and 114b permits the panels 10a and 10b of the headband to more readily flex and conform to the curvature of the wearer's forehead. At the same time, the points or apices 96b, 102b, 108b, and 114b permit the panels 30a and 30b of the visor 30 to flex to the extent needed to provide the curvature that is required from the flexing of the headband 10.

Inasmuch as the wing panels 30c and 30d need not flex as much as the panels 30a and 30b, the tape sections 80 and 86 are differently configured. More specifically, the tape portion 80a of the tape section 80 has edges 116a, 118a and 120a, whereas the portion 80b has edges 116b, 118b, 118c and 120b. The notch 84 facilitates the application of the tape section 80. By the same token, the portion 86a of the tape section 86 has edges 124a, 126a and 128a, and the portion 86b has edges 124b, 126b, 126c and 128b with the notch 90 providing the facile application of the section 86 to the panels 10b and 30d.

Having mentioned the holes 22, it can now be explained that a pair of hooks 130 (only one being visible in FIG. 1) engage in these holes 22, and by reason of an elastic cord 132 extending between the two clips 130, the eyeshade 8 can be readily held in place on the person's head 6. Obviously, the elastic cord 132 can stretch to whatever extent is needed so as to encircle the rear portion of the wearer's head 6. At the same time, however, the headband 10 is flexed so as to conform to the shape of the wearer's forehead. It will be appreciated that whatever curvature is imparted to the headband 10, there automatically follows a flexing of the visor 30 so as to accommodate whatever curvature is imparted to the headband 10, particularly its lower edge 18 which becomes a convexly curved edge in use. The visor 30 has its upper curved edge 32 concavely configured so that it will conform to whatever curvature, even though variable, is assumed by the lower curved edge 18.

Figure 6:
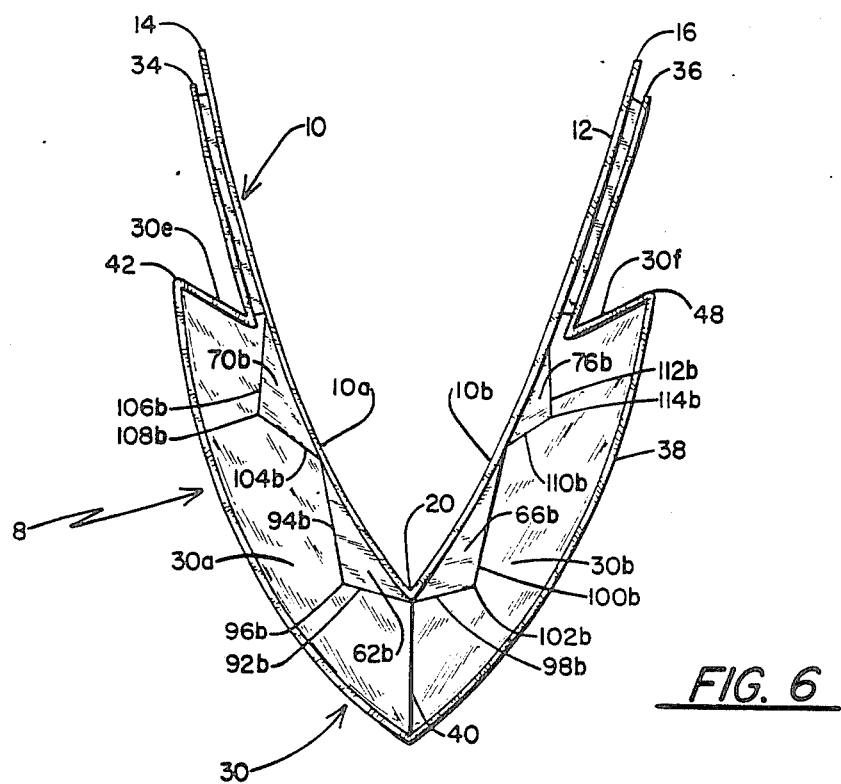
FIG. 6 is a top plan view of the eyeshade in a partially folded condition.
Figure 7:
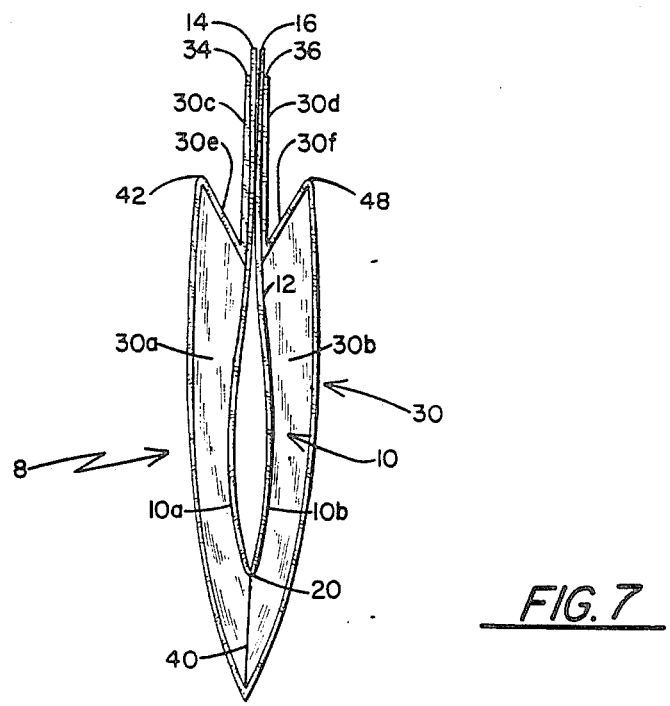
FIG. 7 is a top plan view of the eyeshade when completely folded or collapsed.

It may be well at this point to refer to FIGS. 6 and 7. FIG. 6 illustrates the eyeshade 8 in the process of being folded. In this regard, it will be observed from FIG. 6 that the panels 10a and 10b transitionally assume a V-shaped relationship with each other by reason of the fold line 20 enabling the panels 10a and 10b to be swung into this relationship. Also, it will be observed that the panels 30a and 30b concomitantly assume a V-shaped configuration, but at a more obtuse angle than that of the panels 10a and 10b at this stage of the folding procedure. What is not so obvious is that the fold lines 44 and 50 move inwardly toward the fold line 40. They are permitted to do this by virtue of the fold lines 42 and 48.

While it is not practical to show the entire progressive sequence of folding the eyeshade 8 into the fully folded relationship in which is appears in FIG. 7, it should be noted, though, that the panels 30a and 30b pivot into a confronting relationship with the panels 10a and 10b. Concomitantly with this happening is the fact that the triangular panels 30e and 30f literally confront the marginal portions of the panels 30a and 30b, being permitted to do so by reason of the fold lines 42 and 44 in one instance and the fold lines 48 and 50 in the other. It should also be recognized that the panels 30c and 30d are brought into a confronting relationship with the upper portions of the panels 10a and 10b respectively. It is when the completely collapsed condition of FIG. 7 is reached that the eyeshade 8 can readily be inserted into a person's pocket or into a person's purse. The retrieval of the collapsed or folded eyeshade 8 from either a pocket or purse, as the case maybe, can readily be accomplished because the ends of the panels 10a and 10b having the holes 22 therein are available for easy grasping when the eyeshade 8 is to be used again; the uppermost ends of these panels 10a and 10b, as viewed in FIG. 7, should make this clear.

Although it is believed evident that my eyeshade 8 can be fabricated from paper stock, it should be pointed out that sheet material in the form of a calendered cardboard, such as that used for postcards and file folders, has proved satisfactory in actual practice. Additionally, it should be explained that the cardboard should have a thickness on the order of from 0.012 to 0.015 inch. A basis weight of approximately 135 is desirable, basis weight being pounds per thousand square feet by definition.

Figure 8:
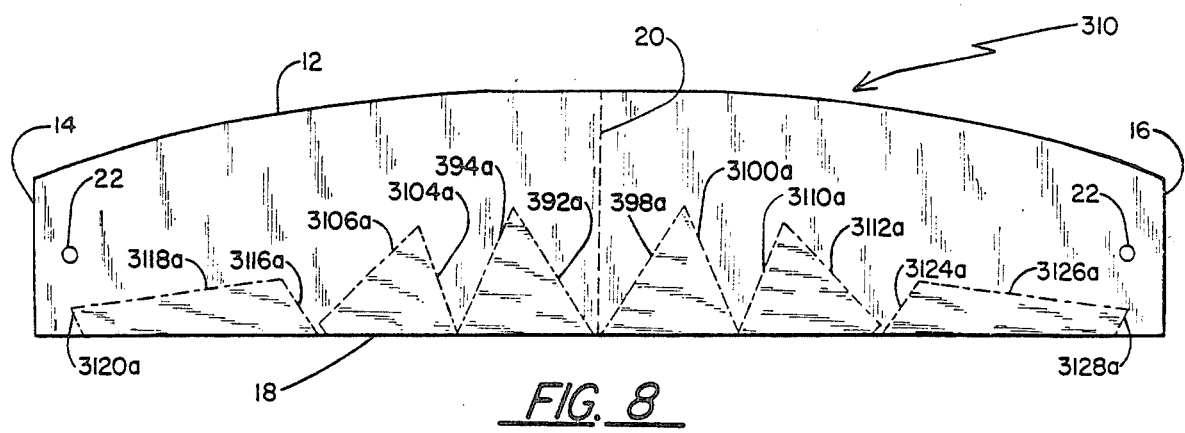
FIG. 8 is a top plan view of the blank that forms the headband, the view looking down on the blank when placed on a horizontal surface.

Referring now to FIG. 8, the cardboard blank that forms the headband 10 has been given the reference numeral 310. Inasmuch as as the edges of the blank 310 correspond to those identified in describing the headband 10, the same reference numerals are employed. The one aspect of the matter that should be recognized is that the edge 18 constitutes a straight line in FIG. 8. It assumes a concavely curved configuration, however, when the blank 310 is incorporated into the eyeshade 8. It is planned that the blank 310 be die cut from the sheet material, more specifically, the cardboard stock having the desired thickness and basis weight.

Inasmuch as the various gummed tape sections 62, 66, 70, 76, 80 and 86 must have their portions 62a, 66a, 70a, 76a, 80a and 86a adhered to the blank 310 at the proper locations, guidelines have been added to FIG. 8, the guidelines appearing in dash/dot form. It perhaps will be of assistance to correlate the guidelines with the edges of the tape sections that have been referred to in describing the assembled eyeshade 8. Therefore, the dash/dot lines have the numeral "3" preceding the numerals used to denote the various edges. The weakened fold line 20 is centrally disposed on the blank 310. At the time the edges of the blank 310 are cut, the holes 22 can be punched.

Figure 9:
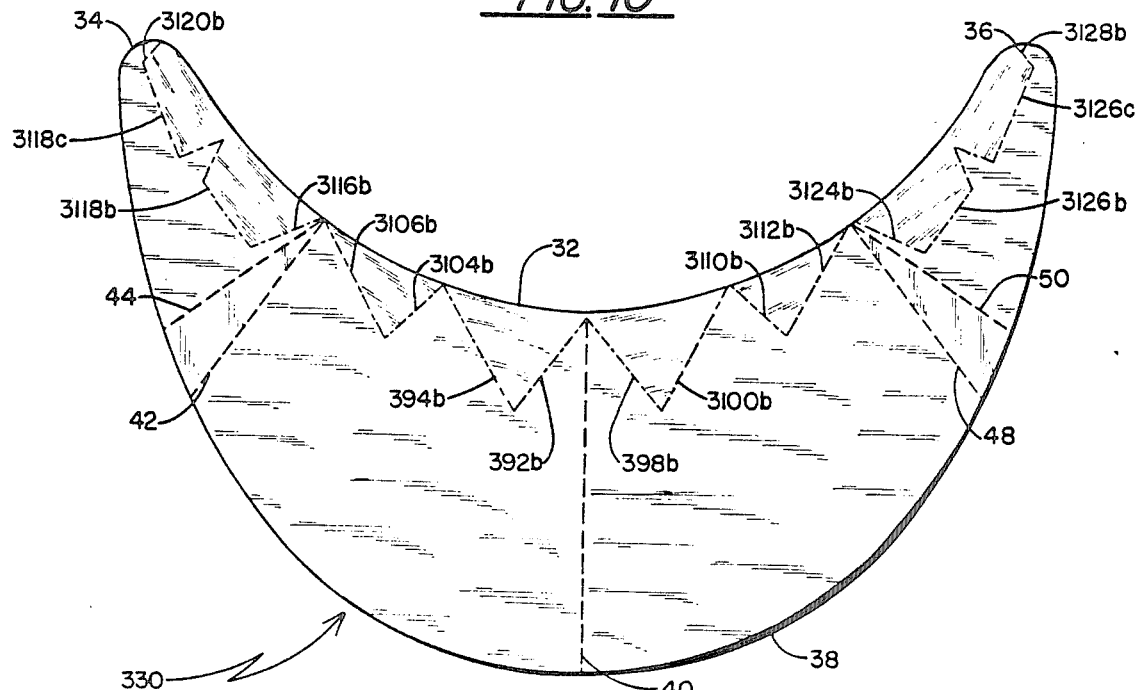
FIG. 9 is a top plan view looking down on the blank that forms the visor.

Turning now to FIG. 9 where the blank 330 that results in the visor 30 is depicted, it will be seen that the same reference numerals have been selected to identify the various edges and fold lines. Here again, however, it will prove helpful, it is believed, to use dash/dot lines to indicate where the portions of the various tape sections are to be adhered. The edges of the various tape sections have already been identified, and the numeral 3 is simply employed so as to indicate where the edges of the tape sections are to be placed when connecting the blank 330 to the blank 310 to constitute the eyeshade 8 comprised of the band 10 and visor 30.

Figure 10:
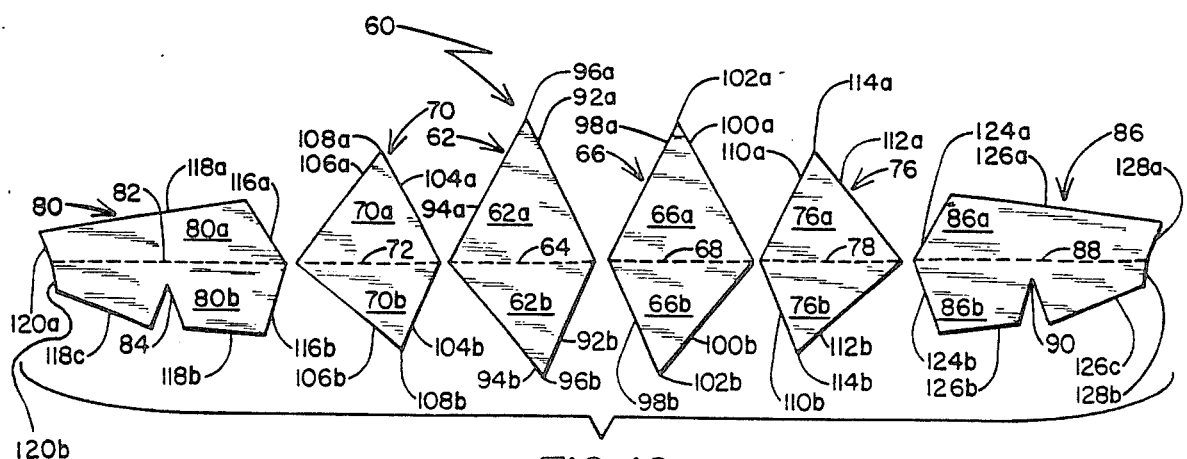
FIG. 10 collectively depicts a series of pressure-sensitive tape sections utilized in connecting the visor to the headband, the view looking down on the sections when resting on a flat surface.

FIG. 10 should be helpful in recognizing the particular shape to be imparted to the various tape sections 62, 66, 70, 76, 80 and 86. Since the edges have already been identified, the same reference numerals are used in FIG. 10 to designate the edges.

In general, it will be appreciated that the various tape sections 62, 66, 70, 76, 80 and 86 are placed in a predetermined relationship or pattern on the blank 310 which becomes the headband 10 and the blank 330 which becomes the visor 30. Care must be exercised to make certain that the tape sections 62 and 70 span the distance between the fold line 40 and the apex 46, whereas the tape sections 66 and 76 span the corresponding distance between the fold line 40 and the apex 52. As previously explained, the triangular configuration imparted to the two portions (identified by the suffixes "a" and "b") of the various tape sections enable the headband 10 and the visor 30 to be readily flexed so that the headband 10 and the visor 30 can assume whatever three-dimensional relationship is needed as far as the person's head 6 is concerned. It will be recognized that the pressure-sensitive tape, frequently called masking tape, should be quite flexible. Tape of this type having a thickness on the order of 0.005 to 0.006 inch has proved satisfactory, it can be explained.

The fold lines 42 and 44 at one side and the fold lines 48 and 50 at the other side are of significant importance because they not only permit a folding to occur at these particular locations, but impart a pleasing appearance to the visor 30 inasmuch as the panels 30a and 30b slope downwardly to a greater degree than the wing panels 30c and 30d.

Consequently, my eyeshade 8 can be inexpensively fabricated from relatively low-cost sheet material, such as cardboard. Not only is the eyeshade 8 attractive when being worn, but can be folded into an extremely compact condition so that it can be readily carried in one's pocket or in one's purse. By the same token, when completely collapsed, such as in FIG. 7, the shipping thereof takes very little space. On the other hand, the eyeshade 8 can be easily unfolded for either a display or an actual use when desired to do so.

It will be appreciated that the various tape sections 62, 64, 70, 76, 80 and 86 can be of one prominent color, such as red, whereas the band 10 can be of, say blue, and the visor 30, for instance, can be white. These colors present a patriotic motif.

On the other hand, the visor 30 has a sufficient surface on which an advertising message can be printed. Even the band 10 has enough open space so that a message can be carried thereon if desired.

The main advantage, however, is that the eyeshade 8, when fabricated in accordance with the present invention, can be conveniently carried so that it is readily available whenever needed to shield one's eyes from the sun or from the glare of artificial lights. My eyeshade 8 will, therefore, be of special benefit at sporting events.

Actually, when advertising messages are printed thereon, the eyeshade 8 can be used as a premium item, being given away at the particular sporting event. Of course, the eyeshade 8 can be used as a premium item in advance of any sporting event, thereby enabling the person who has previously received the eyeshade 8 to carry it with him or her when attending, or participating in, such an event.

Owing to the compact nature that my eyeshade 8 can be folded into, it can be inserted along with various items when being packaged at the factory for later distribution. On the other hand, my eyeshade 8 can serve as a premium item that may be procured by first mailing in a coupon that has been distributed with a particular type of merchandise, my eyeshade 8, owing to its compact size when folded, being easily mailed back in response to the receipt of a such a coupon.

I claim:

1. An eyeshade comprising a headband of sheet material having a first edge and having a central fold line intersecting its said first edge, a visor of sheet material having a second edge complementing the first edge on said headband and having a central fold line intersecting its said second edge, said visor also having a first pair of acutely angled fold lines having their apex spaced to one side of the central fold line on said visor and a second pair of acutely angled fold lines having their apex spaced to the other side of the central fold line on said visor, both of said apices being adjacent the second edge of said visor, and tape means overlying segments of said first and second edges with first portions thereof being secured to portions of said headband and with second portions thereof being secured to portions of said visor to maintain said central fold lines in alignment with each other and to also maintain said apices in a proximal relationship with the first edge of said headband.

2. An eyeshade in accordance with claim 1 in which the first edge on said headband is convexly curved and the second edge of said visor is concavely curved to complement the convexly curved first edge of said headband.

3. An eyeshade in accordance with claim 2 in which said tape means extends between said central fold lines and said apices.

4. An eyeshade in accordance with claim 3 in which said tape means includes respective first and second tape sections located between said central fold lines and said apices, said second tape sections being nearer said apices.

5. An eyeshade in accordance with claim 4 in which said tape means includes respective third tape sections extending in opposite directions from said second tape sections and from said apices.

6. An eyeshade in accordance with claim 4 in which said respective first and second tape sections have converging edges forming spaced points.

7. An eyeshade in accordance with claim 1 in which the sheet material for said headband and visor is cardboard.

8. An eyeshade in accordance with claim 7 in which said tape means is pressure-sensitive masking tape.

9. An eyeshade comprising a headband conformable to the forehead of the wearer, a visor including a central panel portion sloping downwardly and forwardly from a central portion of said headband, and a pair of wing portions flanking the sides of said central portion and sloping downwardly and forwardly at a lesser slope than that of said central portion, said visor additionally including respective triangular portions connecting said wing portions to said central portion, and flexible means connecting said visor to said headband.

10. An eyeshade in accordance with claim 9 in which said headband is formed with a convexly curved lower edge and said visor is formed with a concavely curved upper edge, said flexible means retaining said curved edges in a proximal relation with each other.

11. An eyeshade in accordance with claim 10 in which said flexible connecting means includes sections of gummed tape secured to portions of said headband and said visor.

12. An eyeshade in accordance with claim 11 in which at least some of said tape sections are formed with laterally spaced points.

13. A collapsed eyeshade of flexible sheet material comprising a headband having a first pair of confronting panels with a fold line therebetween, a visor having a second pair of panels with a fold line therebetween, portions of said second pair of panels confronting portions of said first pair of panels, a third pair of panels connected to said second pair of panels by means of additional fold lines, said third pair of panels being triangularly shaped and respectively residing between portions of said first and second pairs of panels and confronting said second pair of panels, a fourth pair of panels connected to said third pair of panels by means of still additional fold lines, said fourth pair of panels having portions respectively residing between said third panels and confronting said first pair of panels, and tape means secured to said first, second and fourth pairs of panels.

14. An eyeshade in accordance with claim 13 in which said flexible sheet material is cardboard and said tape means includes sections of pressure-sensitive masking tape.

15. An eyeshade in accordance with claim 14 in which said cardboard has a thickness on the order of from 0.012 to 0.015 inch and said masking tape has a thickness on the order of from 0.005 to 0.006 inch.

* * * * *